United States Patent [19]

Diller et al.

[11] 4,271,121
[45] Jun. 2, 1981

[54] PLAQUE FOR MEASURING THE DOSE OF REACTIVE GASES

[75] Inventors: Werner Diller, Leverkusen; Eckard Drope, Cologne; Günther Ellendt; Ernst Reichold, both of Krefeld all of Fed. Rep. of Germany

[73] Assignee: Bayer Aktiengesellschaft, Leverkusen, Fed. Rep. of Germany

[21] Appl. No.: 75,376

[22] Filed: Sep. 13, 1979

[30] Foreign Application Priority Data

Sep. 27, 1978 [DE] Fed. Rep. of Germany ....... 2841991

[51] Int. Cl.³ .......................... G01N 1/48; G01N 21/06
[52] U.S. Cl. ........................................ 422/56; 422/58; 422/57; 116/206; 252/408
[58] Field of Search ..................................... 422/55–58, 422/86–88, 119; 73/23; 252/408; 116/206

[56] References Cited

U.S. PATENT DOCUMENTS

| | | | |
|---|---|---|---|
| 2,249,867 | 7/1941 | Snelling | 422/56 |
| 3,480,402 | 11/1969 | Jackson | 422/56 |
| 3,723,064 | 3/1973 | Liotta | 422/56 |
| 4,195,056 | 3/1980 | Patel | 422/56 |

OTHER PUBLICATIONS

Jacobs, M. B., *The Analytical Chemistry of Industrial Poisons, Hazards, and Solvents,* Interscience Publishers, Inc., New York, 1949.

*Primary Examiner*—William F. Smith
*Assistant Examiner*—Chris Konkol
*Attorney, Agent, or Firm*—Sprung, Felfe, Horn, Lynch & Kramer

[57] ABSTRACT

Plaques for rapid retrospective recognition of an overdose of noxious gases are of great importance for industrial protection in the chemical industry. These plaques carry an indicator which undergoes a color change on exposure to the gas. Visual assessment of the indicator is considerably facilitated by subdivision of the indicator surface into a plurality of measuring fields with graded sensitivity by means of different covering membranes. Rapid allocation to a given range of dose is possible by separate or combined visual observation of the individual fields of the indicator.

2 Claims, 2 Drawing Figures

PLAQUE FOR MEASURING THE DOSE OF REACTIVE GASES

BACKGROUND OF THE INVENTION

This invention relates to a plaque for the rapid recognition of a dose of reactive and in particular of noxious gases by means of an indicator which undergoes a colour change on exposure to the gas. Such plaque may be used, for example, to obtain a retrospective reading of the dose of a noxious gas at a work-place. For this purpose, the plaque is attached to the work clothing of a person and carried during the whole working day. The indicator undergoes a characteristic colour change on exposure to a toxic gas. The intensity of the colour is normally proportional to $\lg \int c\, dt$, where c is the concentration of the gas and t is the time. If a colour change occurs, the person carrying the plaque must immediately report to the doctor.

The colour change of the indicator has in the past been compared with a standard. Since such a method of assessment is time consuming and requires the use of apparatus, there is the risk that cases of poisoning may not be recognized sufficiently quickly. To enable the doctor to initiate optimum therapy at an early stage, he requires information on the possible dose inhaled.

SUMMARY OF THE INVENTION

It is therefore an object of the present invention to develop a plaque which can be interpreted simply and rapidly without technical aids. In a plaque with a colour indicator, this problem is solved by sub-dividing the surface of the indicator into several measuring fields by covering it with membranes which are graded in their sensitivity so that rapid correlation with different ranges of dose can be achieved by separate or combined visual examination of the individual indicator fields. This grading of the area of measurement is effected in practice by masking the indicator fields with membranes which differ in their diffusion resistance. The resistance to diffusion is proportional to the thickness of the membrane and its diffusion coefficient. By "membranes" are meant laminated, gas permable, porous bodies such as, for example, paper, gas permeable foils or porous plates of ceramics or sintered metal.

Each indicator field preferably has its own window in the plaque.

Advantages of the invention lie in the fact that after an exposure, the plaque can be assessed virtually at a glance. In physical terms, the sub-division of the indicator into fields of graded sensitivity means the possibility of digitalizing the result, as opposed to analogous photometric assessment. In addition, the novel plaque has the advantage of being simple and inexpensive to manufacture.

According to the present invention, there is provided a plaque for rapid recognition of a dose of reactive gas, said plaque comprising an indicator, which undergoes a colour change on exposure to the gas, wherein the indicator surface is subdivided into a plurality of measuring fields by different coverings of membranes, the sensitivity of which fields is chosen so that rapid correlation to given ranges of doses can be achieved by separate or combined visual examination of the individual indicator fields.

BRIEF DESCRIPTION OF THE DRAWINGS

An embodiment of the invention given by way of example is described in more detail below with reference to the accompanying drawings, in which.

DETAILED DESCRIPTION OF THE INVENTION

Figure 1:
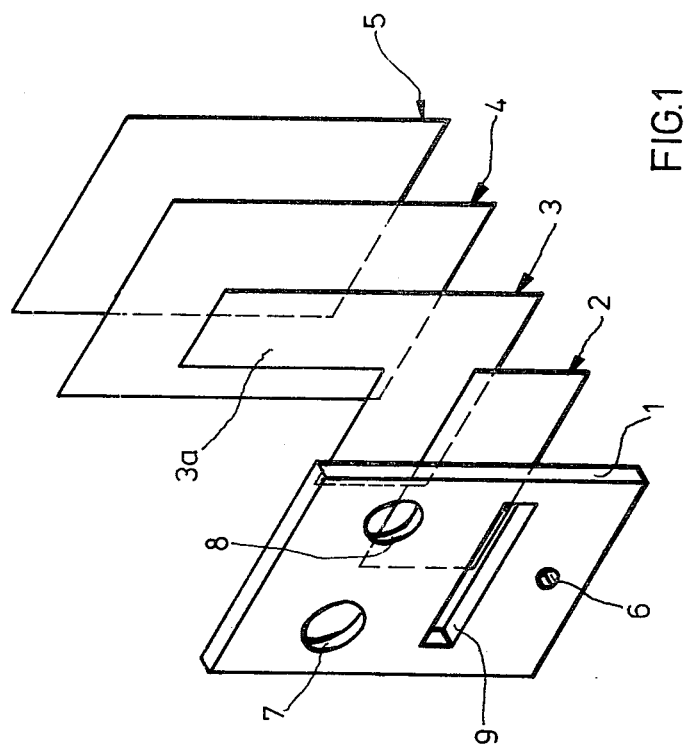
FIG. 1 is an exploded view of a plaque for phosgene determination.

The plaque of FIG. 1 comprises a front wall 1, covering membranes 2 and 3, an indicator 4 and a rear wall 5. To assemble this plaque, the indicator 4 with the covering membranes 2 and 3 over it are placed into the rear wall 5, and the front wall 1 is then placed in position and fixed with a screw 6. The plaque is of such a size that it can easily be attached to the clothing of a person by means of a pin inserted in the rear wall.

For phosgene determination, the indicator 4 may comprise a paper strip impregnated with 4-(4'-nitrobenzyl)-pyridine and N-phenyl benzylamine. The action of phosgene on this indicator produces a red colouration the intensity of which is logarithmically proportional to the product of the phosgene concentration and the time of exposure (dose). The front wall 1 has three windows differing in size and geometry: a circular aperture 7 of large diameter and a circular aperture 8 of smaller diameter, and a rectangular aperture 9. The covering membranes 2 and 3, made, for example, of filter paper, cover different partial areas of the indicator 4. The indicator field behind the circular window 7 is left free, i.e. it is not covered at all. The indicator field corresponding to the smaller circular window 8 is masked only by an upper extension 3a of membrane 3 while the indicator field corresponding to the rectangular window 9 is covered both by the rectangular membrane 2 and by a lower, rectangular part of membrane 3. In the presence of a phosgene concentration, therefore, the indicator 4 is directly exposed to the phosgene through the window 7 while the effect of phosgene acting on the indicator fields situated behind the windows 8 and 9 is attenuated step-wise by the membranes 2 and 3. This attenuation is due to the diffusion resistance of the membranes. The indicator 4 is thus sub-divided into measurement areas differing in their sensitivity. The field corresponding to window 7 is the most sensitive area of measurement while the field corresponding to window 9 is the least sensitive. Subdivision of the indicator surface into different areas of measurement is most simply carried out as shown here by covering the surface with membranes of different thicknesses or with a graded number of membrane elements.

The range of measurement and the grading of the individual fields are so chosen that rapid correlation to given ranges of dose can be carried out by separate or combined visual examination of the individual fields. The ranges into which the doses are sub-divided, for example, in the case of phosgene, is laid down according to a typical correlation between phosgene poisoning and dose which manifests itself clinically in the following manner:

1. 0–1 ppm min: no exposure;
2. 1–70 ppm min: slight signs of irritation; on the whole, no risk attached to the exposure;
3. 70–300 ppm min: signs of histological oedema, exposure harmful to health;

4. >300 ppm min: clinically manifest pulmonary oedema; exposure endangers life.

Figure 2:
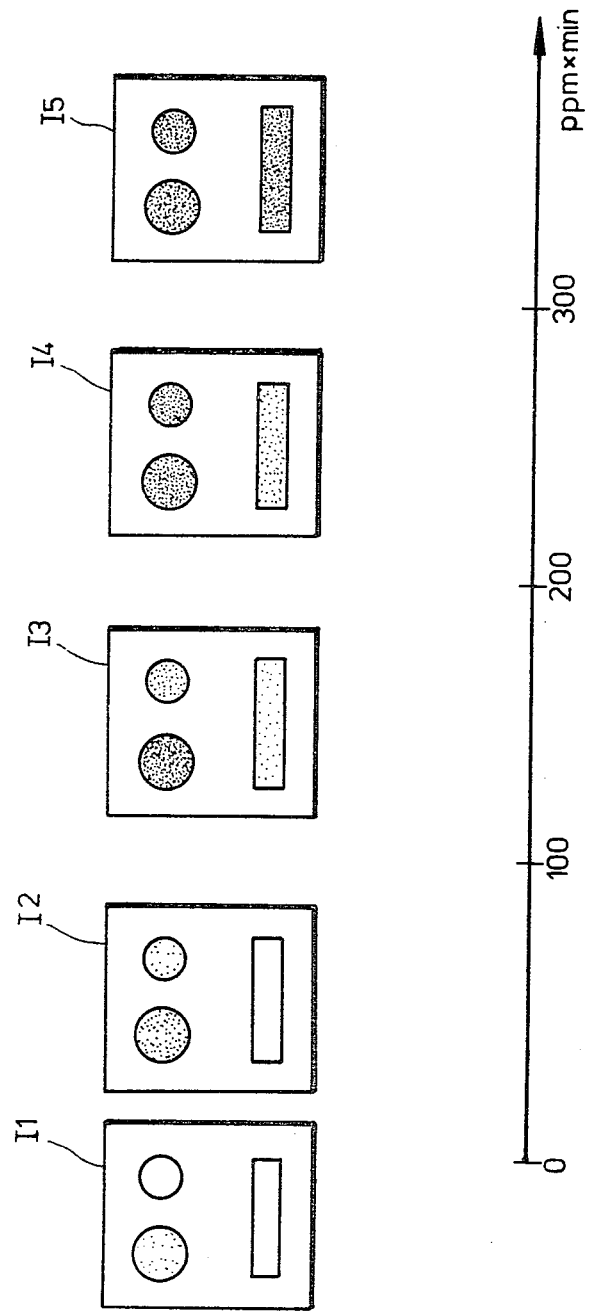
FIG. 2 represent various stages of exposure of the phosgene indicator.

FIG. 2 shows indicators $I_1$ to $I_5$ exposed inside a plaque of FIG. 1 to different doses of phosgene increasing step-wise from left to right. The results are summarised in the following table.

| Indicator | Dose | | Visual assessment of fields |
| --- | --- | --- | --- |
|  |  | ○ | onset of red colouration |
| $I_1$ | <5 ppm min | ○ | no red colouration |
|  |  | ▭ | no red colouration |
| $I_2$ | 50–80 ppm min | ○ | moderate red colouration |
|  |  | ○ | onset of red colouration |
|  |  | ▭ | no red colouration |
| $I_3$ | 100–150 ppm min | ○ | strong red colouration |
|  |  | ○ | moderate red colouration |
|  |  | ▭ | onset of red colouration |
| $I_4$ | 200–250 ppm min | ○ | strong red colouration |
|  |  | ○ | strong red colouration |
|  |  | ▭ | moderate red colouration |
| $I_5$ | >300 ppm min | ○ | strong red colouration |
|  |  | ○ | strong red colouration |
|  |  | ▭ | strong red colouration |

It will be seen from this example that the subdivision of an indicator into measuring fields differing in sensitivity makes rapid and reliable correlation of a certain exposure to one of the given ranges of doses possible. This advantage is particularly convenient in the case of severe exposure in the range of 200–400 ppm min because in that range the difference in colour density progressively decreases with increasing dose. No comparison standard is required. In this way, the medical staff can classify the exposure upon presentation of the plaque without the aid of apparatus and can immediately initiate the correct therapeutical measures.

The plaque according to the invention is by no means limited to medical diagnostic applications. It may be used, for example, for monitoring and retrospectively determining the dose of a corrosive atmosphere to which a machine or sensitive structural element has been exposed. In the case of claims for damages, for example, the manufacturer of a machine can establish retrospectively whether the machine has been in operation in an excessively corrosive atmosphere.

We claim:

1. A plaque for the rapid recognition of a dose of reactive gases comprising: a front wall having at least three windows therein; a rear wall having the same outer configuration as the front wall; an impregnated indicator strip between the front wall and the rear wall configured to overlie all of the windows and capable of undergoing a color change upon exposure to a gas; and superposed membrane layers disposed between the front wall and the indicator strip and configured such that the indicator strip is directly exposed to the atmosphere at a first window, is masked with a single membrane layer at a second window and is masked with two superimposed membrane layers at the third window to produce fields of stepwise graded sensitivity on the indicator strip whereby a rapid correlation to given ranges of doses can be achieved by a combined visual examination of the individual indicator fields.

2. The plaque according to claim 1 for the measurement of phosgene, wherein the indicator strip comprises a paper strip impregnated with 4-(4′nitrobenzyl)pyridine and N-phenyl benzylamine.

* * * * *